United States Patent
Hangya et al.

(10) Patent No.: US 10,231,826 B2
(45) Date of Patent: Mar. 19, 2019

(54) PRELOADED INJECTOR WITH ROTATABLE MEMBER FOR STORING AND INJECTING HYDROPHOBIC INTRA OCULAR LENSES

(71) Applicant: MEDICONTUR ORVOSTECHNIKAI KFT, Zsambek (HU)

(72) Inventors: Peter Hangya, Bicske (HU); Laszlo Kontur, Budapest (HU)

(73) Assignee: Medicontur Orvostechnikal Kft, Zsambek (HU)

( * ) Notice: Subject to any disclaimer, the term of this patent is extended or adjusted under 35 U.S.C. 154(b) by 275 days.

(21) Appl. No.: 15/037,904

(22) PCT Filed: Nov. 20, 2013

(86) PCT No.: PCT/HU2013/000108
§ 371 (c)(1),
(2) Date: May 19, 2016

(87) PCT Pub. No.: WO2015/075488
PCT Pub. Date: May 28, 2015

(65) Prior Publication Data
US 2016/0287382 A1    Oct. 6, 2016

(51) Int. Cl.
*A61F 2/16*    (2006.01)

(52) U.S. Cl.
CPC ............ *A61F 2/1664* (2013.01); *A61F 2/167* (2013.01); *A61F 2/1678* (2013.01)

(58) Field of Classification Search
CPC ...... A61F 2/1644; A61F 2/167; A61F 2/1678; A61B 17/128; A61B 17/105
See application file for complete search history.

(56) References Cited

U.S. PATENT DOCUMENTS

| | | | | |
|---|---|---|---|---|
| 5,304,182 A | * | 4/1994 | Rheinish | A61F 2/167 128/898 |
| 5,772,666 A | * | 6/1998 | Feingold | A61F 2/1664 606/107 |
| 5,944,725 A | * | 8/1999 | Cicenas | A61F 2/1678 606/107 |
| 5,947,975 A | | 9/1999 | Kikuchi et al. | |

(Continued)

FOREIGN PATENT DOCUMENTS

| | | |
|---|---|---|
| EP | 2 111 820 A1 | 10/2009 |
| WO | 2007/078602 A2 | 7/2007 |

OTHER PUBLICATIONS

International Search Report dated Jul. 18, 2014 in PCT/HU2013/000108 Filed Nov. 20, 2013.

*Primary Examiner* — Alexander Orkin
(74) *Attorney, Agent, or Firm* — Olson & Cepuritis, Ltd.

(57) ABSTRACT

A preloaded injector for storing and injecting hydrophobic intra ocular lenses (IOL) comprises a plunger (2), an injector body (12), an adapter (16), a rotatable member (18), a cartridge (20) with a nozzle tube (22) and a stopper (26). The rotatable member (18) is provided around the cartridge (20) for setting the cartridge (20) from an open position to a closed position. The rotatable member (18) is furnished with a portion interfering with a portion of the stopper (26) keeping the stopper (26) irremovable in its first position but releasing the stopper (26) in its second position.

5 Claims, 5 Drawing Sheets

(56) References Cited

U.S. PATENT DOCUMENTS

| | | | |
|---|---|---|---|
| 8,403,941 B2* | 3/2013 | Peterson | A61F 2/1691 606/107 |
| 2001/0014808 A1 | 8/2001 | Kikuchi et al. | |
| 2003/0036765 A1* | 2/2003 | Van Noy | A61F 2/1678 606/107 |
| 2004/0243141 A1* | 12/2004 | Brown | A61F 2/1678 606/107 |
| 2005/0049605 A1* | 3/2005 | Vaquero | A61F 2/1678 606/107 |
| 2007/0150054 A1 | 6/2007 | Pynson | |
| 2008/0058830 A1* | 3/2008 | Cole | A61F 2/1664 606/107 |
| 2011/0137321 A1 | 6/2011 | Pynson | |
| 2011/0172766 A1 | 7/2011 | Pynson | |
| 2012/0016374 A1* | 1/2012 | Han | A61F 2/1678 606/107 |
| 2013/0041382 A1* | 2/2013 | Ben Nun | A61F 2/1678 606/107 |

\* cited by examiner

PRELOADED INJECTOR WITH ROTATABLE MEMBER FOR STORING AND INJECTING HYDROPHOBIC INTRA OCULAR LENSES

CROSS-REFERENCE TO RELATED APPLICATION

This application is a U.S. National Stage of PCT/HU2013/000108, filed Nov. 20, 2013, which is incorporated herein by reference.

TECHNICAL FIELD

The present invention relates to a surgical injector more particularly, the present invention relates to a preloaded injector with rotatable member for storing and injecting hydrophobic intra ocular lenses (IOL).

BACKGROUND

An IOL is an artificial lens implanted in the eye, for example, as a replacement for the natural crystalline lens after cataract surgery or to alter the optical properties of an eye in which the natural lens remains. IOLs include an optic, and preferably at least one flexible fixation member or haptic which extends from the optic and becomes affixed in the eye to secure the lens in position. The optic normally includes an optically clear lens. Implantation of such IOLs into the eye involves making an incision in the eye. It is advantageous, to reduce trauma and speed healing, to have an incision size as small as possible. Some IOLs are foldable so that the IOL can be inserted through a smaller incision into the eye. A variety of instruments have been proposed to aid in inserting such a foldable lens in the eye.

In one method, the surgeon simply uses surgical forceps having opposing blades which are used to grasp the IOL and insert it through the incision into the eye. While this method is still practiced today, more and more surgeons are using more sophisticated IOL inserter devices which offer advantages such as affording the surgeon more control when inserting the IOL into the eye. IOL inserter devices, so called injectors, have recently been developed with reduced diameter nozzles which allow for a much smaller incision to be made in the cornea than is possible using forceps alone. Smaller incision sizes (e. g., less than about 3 mm) are preferred over larger incisions (e. g., about 3.2 to 5+mm) since smaller incisions have been attributed to reduced post-surgical healing time and complications such as induced astigmatism.

The IOL may be made from a variety of materials or combination of materials such as PMMA, silicone, hydrogels and silicone hydrogels, etc.

Two types of IDLs can be distinguished regarding the storage thereof. The hydrophilic IOLs have to be stored in fluid solvent in a container and are loaded to the injector just before inserting them into the eye. In contrast, hydrophobic IDLs can be stored in a cartridge in a dry environment.

In case of hydrophilic IOLs, the IOL must first be loaded into the IOL injector. The loading of the IOL into the injector is therefore a precise and very important step in the process. An example of hydrophilic IOL and injector thereof can be seen in patent specification US2010280521 in which a retainer is provided for holding an IOL in an unstressed state. Before injection, the retainer and IOL are attached to an injector body and a compressor is moved to the closed position to compress the IOL. During injection, the compressor remains on the injector body.

In the patent specification WO2007078602, an apparatus is described for loading a hydrophilic IOL into an injector. The IOL is stored in a vial and is fixed by holder mounts. In course of loading, the vial is pushed to the injector comprising a loading chamber. The loading chamber has a component that when being closed folds the lens. The goal of the apparatus is to prevent the damage of the IOL during loading.

In case of hydrophobic IOLs, the IOL are stored together with the injector and there is no need of loading. Such a construction is described in patent specification EP1481652. Since the IOL is stored in the injector, special provision is needed to prevent a premature injection. Therefore a stop means shall be applied for stopping the movement of the IOL prior to the usage, during shipment and storage. The stop means is frictionally engaged on the lid of the injector, so an accidental removal can release the IOL to be injected.

Unfortunately, providing the injector with additional elements for further decreasing the risk of premature injection would result in a clumsy construction which would disturb the surgeon during injection of the IOL.

As it is seen from the description above, the preparation of hydrophobic IOLs for injection is a complex problem in which the preloaded IOL shall be folded as well as prevent premature injection. Constructions for hydrophilic IOL cannot be used due to the different way of loading and the different characteristic of the hydrophobic lenses. Therefore, there is a need for development of alternative solutions for a preloaded injector that would provide an injection of hydrophobic IOLs in which the folding of the IOL should be carried out in a cartridge prior to the injection but the premature injection is prevented.

SUMMARY

We have set ourselves the objective with this invention to improve the injectors for IOLs in order to solve at least some of the aforementioned problems, by the usage of a special element that folds the IOL and can be removed before injection. Additionally the special element combines the function of folding the IOL with a double locking mechanism.

Accordingly, the invention relates to a preloaded injector with rotatable member for storing and injecting hydrophobic intra ocular lenses (IOL). The injector comprises an injector body accommodating a plunger adapted to reciprocate within the injector body. A cartridge with a nozzle tube is attached to the injector body, and furnished with a winglet adapted to hinge between an open and a closed position. The cartridge is adapted to hold the IOL in a released state in case of the open position and to cause the IOL to fold in case of the closed position. A stopper prevents the plunger to move in the injector body prior to injecting. A rotatable member is provided around the cartridge for setting the cartridge from the open position to the closed position when the rotatable member is rotated from a first position to a second position. The rotatable member is furnished with a portion interfering with a portion of the stopper keeping the stopper irremovable in its first position but releasing the stopper in its second position.

Due to the interaction of the rotatable member and the stopper, a double locking mechanism is established providing enhanced safeguard against premature injection by preventing the stopper to be removed before closing the cartridge.

This construction allows the IOL to be folded for injection without any manipulation. Additionally, in the closed position of the cartridge, the rotatable member, which made the closing of the cartridge easier but is unnecessary in the further operations, can be removed.

BRIEF DESCRIPTION OF THE DRAWINGS

For a more complete understanding of the invention, reference is made to the following detailed description of an embodiment taken in conjunction with the accompanying drawings wherein.

DETAILED DESCRIPTION

In the following, for purpose of explanation and not limitation, specific details of an injector for IOLs are set forth, in order to provide a thorough understanding of the present invention. It will be apparent to one skilled in the art that the present invention may be practiced in other embodiments that depart from these specific details.

Figure 1:
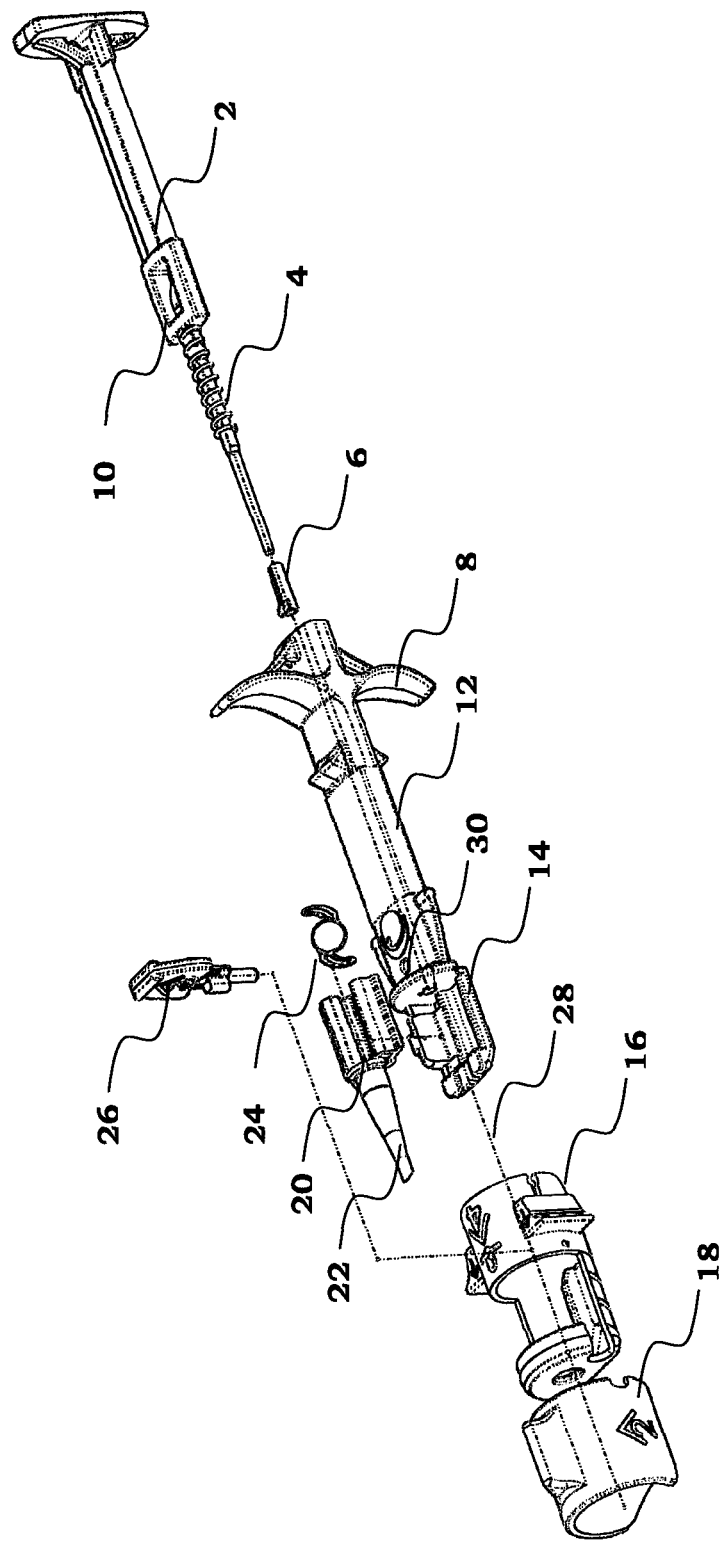
FIG. 1 shows the parts of an embodiment of the injector in perspective view.

As it is shown in FIG. 1, the injector may comprise a plunger 2, an injector body 12, an adapter 16, a rotatable member 18, a cartridge 20 with a nozzle tube 22 and a stopper 26. The injector body 12 accommodates the plunger 2 adapted to reciprocate within the injector body 12. The plunger 2 is furnished with a locker 10 and with a spring 4. Additionally a soft tip 6 is inserted to one end of the plunger 2. The injector body 12 may be provided with a finger hold flange 8 and a docking portion 14 at its end close to the cartridge. The adapter 16 can be a sleeve with rails providing connections between the rotatable member 18 and the injector body 12. The rotatable member 18 can be a ring but any other form of construction is suitable that can turn around the axis 28 of the injector. The cartridge 20 and the nozzle tube 22 are molded in a single piece in this embodiment but they can be formed in two distinct pieces too. The cartridge 20 with a nozzle tube 22 can be attached to the injector body 12. The IOL 24 is placed in the cartridge 20. The lower portion of the stopper 26 can be plugged into a hole 30 of the injector body 12 through the adapter 16 preventing the plunger 2 to reciprocate in the injector body 12 prior to injecting.

The reassembling steps of the injector are as follows.
attaching the cartridge 20 with the IOL 24 to the injector body 12,
pulling the spring 4 and the soft tip 6 onto the plunger 2
inserting the plunger 2 into the injector body 12,
attaching the adapter 16 to the injector body 12,
inserting the stopper 26 through a hole 30 across the injector body 12 and the plunger 2,
pulling the rotatable member 18 on the adapter 16.

Figure 2:
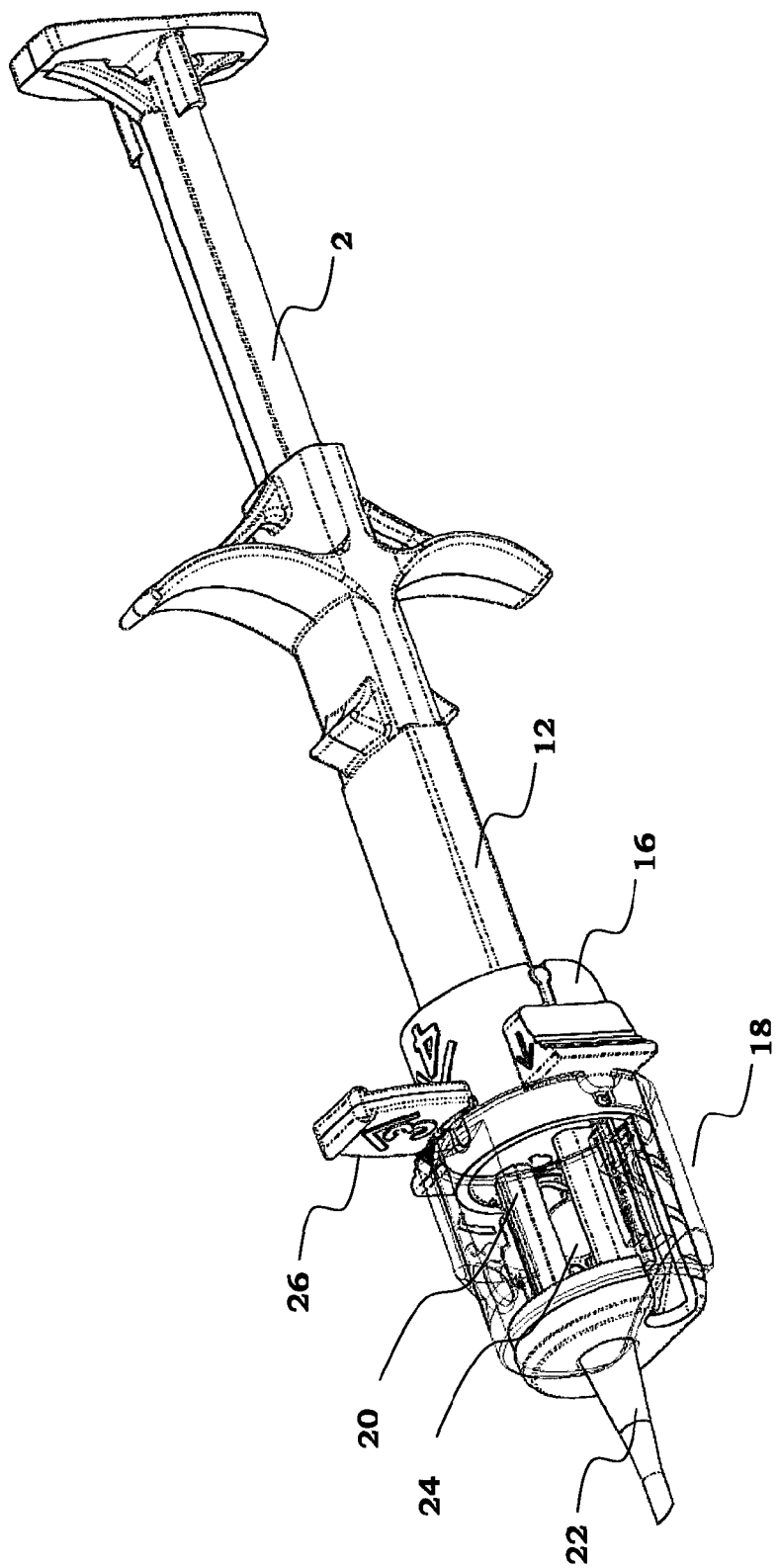
FIG. 2 depicts the complete injector in perspective view.

In FIG. 2, the injector can be seen after reassembling. In this state, the plunger 2, the adapter 16 and the rotatable member 18 are fixed to the injector body 12 and are immobilized by the stopper 26. The rotatable member 18 is depicted in a transparent manner in order to show the position of the IOL 24 in the cartridge 20. The IOL 24 is kept in the cartridge 20 in a released state and together with the injector they are ready for packaging and for putting to the market.

FIGS. 3A to 3D show the preparation steps before use of the injector depicting only the end of the injector with a part of the injector body 12, the stopper 26, the adapter 16, the rotatable member 18 and the nozzle tube 22. The correct order of steps is shown by pictograms and numbers indicated on the surface of the rotatable member 18, the stopper 26 and the adapter 16.

Figure 3B:
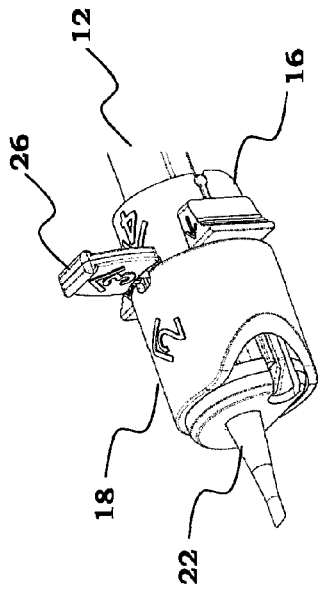
FIGS. 3A, 3B, 3C, and 3D show the consecutive phases of preparation before injection.
Figure 3A:
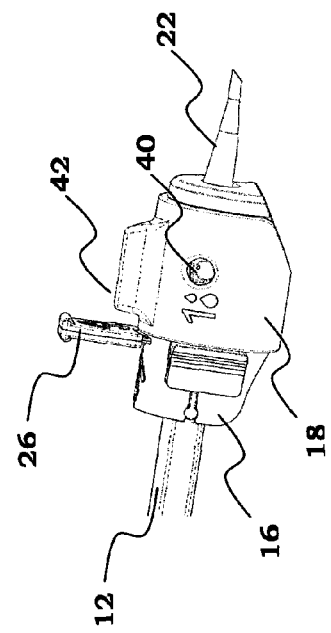

As it is seen in FIG. 3A number "1" informs the surgeon first to inject visco elastic material into a hole 40 on the rotatable member 18. After injection of the visco elastic material, the rotatable member 18 has to be turned around the axis of the injector. Turning around can be made easier by means of a protrusion 42 mounted on the outer surface of the rotatable member 18.

FIG. 3B illustrates the next step in which the rotatable member 18 is turned around. This step is indicated by a number "2" with an arrow above "⌒", showing the direction of turning. By turning around, the rotatable member 18 around the cartridge is rotated from a first position to a second position by which the cartridge is made from an open position to a closed position. If the cartridge is closed, it cannot be opened any more. The closing of the cartridge will be described later in FIGS. 6A, and 6B.

Figure 3D:
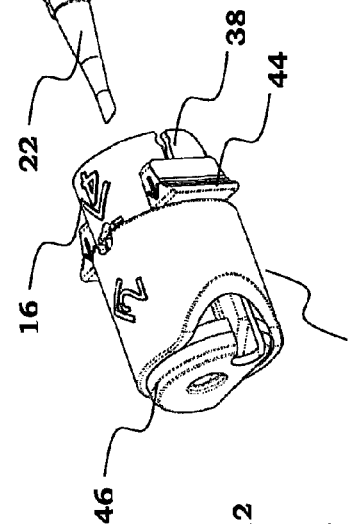
Figure 3C:
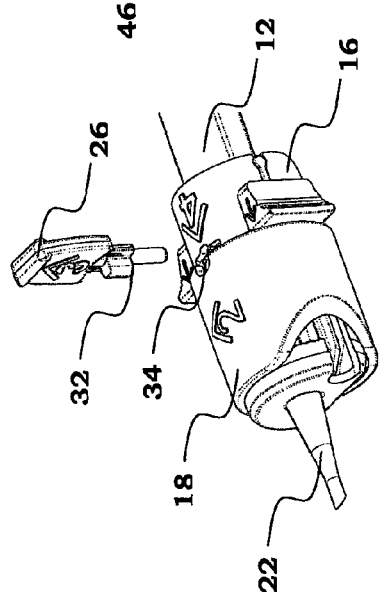

In FIG. 3C, the next step can be seen when the stopper 26 is removed. Since the rotatable member 18 is furnished with a portion interfering with a portion of the stopper 26 keeping the stopper 26 irremovable in the first position of the rotatable member 18 but releasing the stopper 26 in its second position. This step is indicated by a number "3" with an arrow above "⌒", showing the direction of removing. Removing can be carried out just because interfering portions such as a recess 34 on the edge of the rotatable member 18 fits to a protrusion 32 mounted on the leg of the stopper 26. It can be highlighted that rotation of the rotatable member 18 has double functions, i.e. it closes the cartridge and releases the stopper 26.

The final step is shown in FIG. 3D in which the adapter 16 and the rotatable member 18 are removed from the cartridge 20 and the injector body 12. The step is indicated by a number of "4" with an arrow above "⌒" on the surface of the adapter 16. Another arrow depicted on a protrusion 44 on the outer surface of the adapter 16 shows the direction of removing. After removing it can be seen that the adapter 16 staying between the cartridge 20 and the rotatable member 18 is provided with rails both for connection to the injector body 12 and to the rotatable member 18. The rail to the injector body 12 can be a groove 38 fitting to a feather 36 on the injector body 12 longitudinal to the axis 28 of the injector. The rail to the rotatable member 18 can be a ring shaped stop-shoulder 46 around the outer surface of the adapter 16. If the rotatable member 18 is shaped as a conical ring, and the inner diameter of the ring at the end close to the stop-shoulder 46 is smaller than the outer diameter of the stop-shoulder 46, the adapter 16 and the rotatable member 18 are fixed to each other and they can be removed from the injector body 12 together only.

Figure 4:
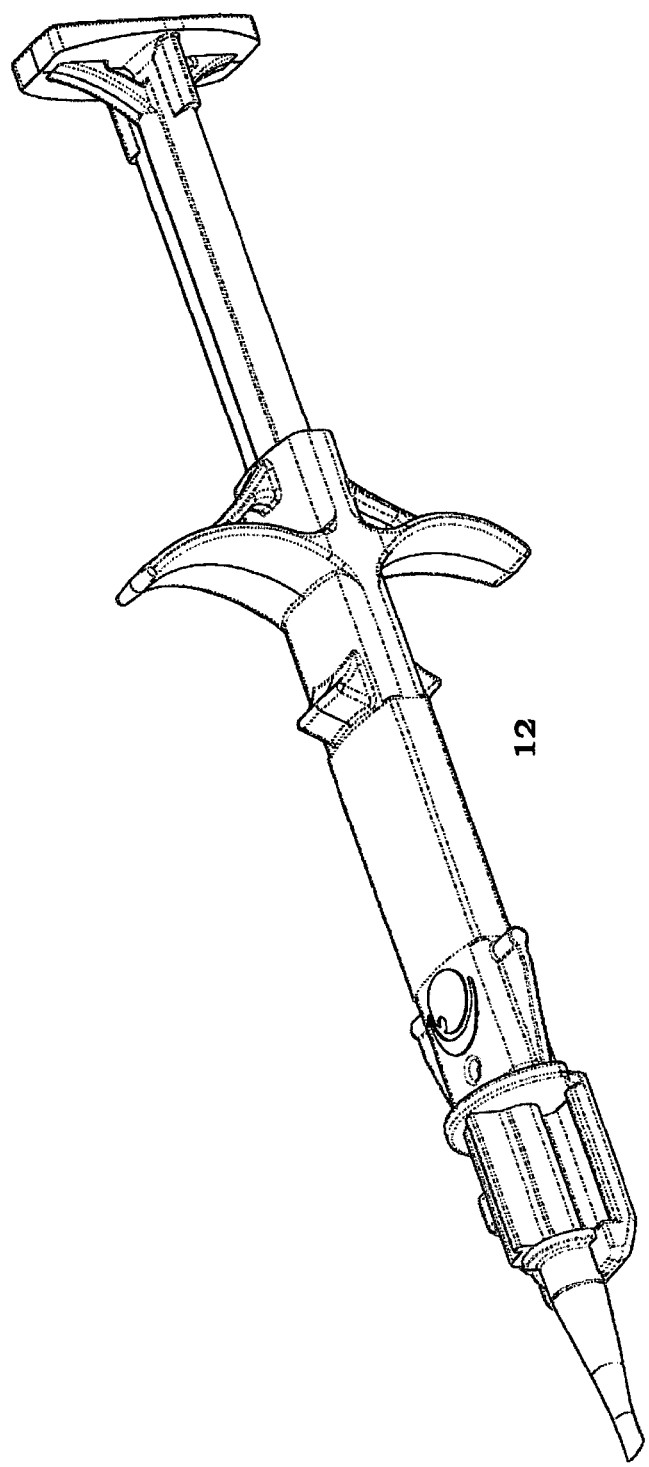
FIG. 4 illustrates the injector ready for injection in perspective view.

In FIG. 4, the injector can be seen ready for injection. After removing the rotatable member 18 with the adapter 16, the injector may comprise the plunger 2, the injector body 12 and the closed cartridge 20 with the nozzle tube 22 only. In this state the injector possesses the necessary elements only for the injection without any elements that are not needed any more.

Figure 5:
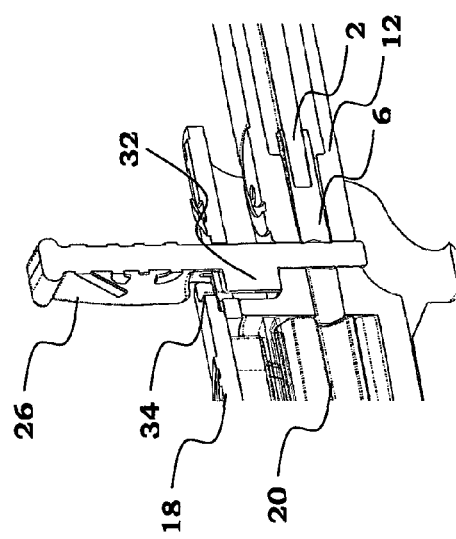
FIG. 5 depicts a sectional view about the position of the stopper in the injector.

FIG. 5 illustrates an axial sectional view of the relation among the stopper 26, the rotatable member 18, the cartridge 20 and the injector body 12 in that phase in which the rotatable member 18 is turned to its second position in course of closing the cartridge 20. The soft tip 6 attached to the end of the plunger 2 is stopped by the stopper 26 preventing any premature injection. The injection is allowed when the stopper 26 is removed. The removal of the stopper 26 is possible since by turning the rotatable member 18 to its second position, the recess 34 on its edge is positioned just above the protrusion 32 of the stopper 26. In the first position of the rotatable member 18, the recess 34 does not lay above the protrusion 32 so it is not possible to remove the stopper 26. In this way a double locking mechanism is established providing enhanced safeguard against premature injection. I.e.

1) the plunger 2 cannot be reciprocated in the injection body 12 before removal of the stopper 26;

2) the stopper 26 cannot be removed before rotating the rotatable member 18 to its second position and thereby closing the cartridge 20.

During injection the plunger 2 is pushed in the injector body 12 whereby the soft tip 6 reaches the IOL 24 and makes it move from the cartridge 20 through the nozzle tube 22 to the outer space. The soft tip 6 is made of an elastic material dynamically fitting to the interior of the cartridge 20 and the nozzle tube 22 during the injection. The locker 10 on the plunger 2 is adapted to bump at the end of the injector body 12 just before the soft tip 6 arrives at the distal end of the nozzle tube 22, preventing the soft tip 6 leaving the nozzle tube 22 during the injection.

Figure 6A:
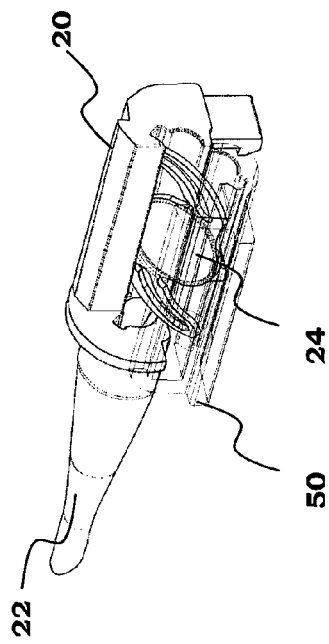
FIGS. 6A and 6B illustrate the cartridge with the IOL in open and close position.

FIG. 6A, shows the cartridge 20 with the nozzle tube 22 holding the IOL 24. The cartridge 20 has a winglet 50 that can hinge on the cartridge 20. The winglet 50 is open i.e. the cartridge is in open position so the IOL 24 is in a released state.

Figure 6B:
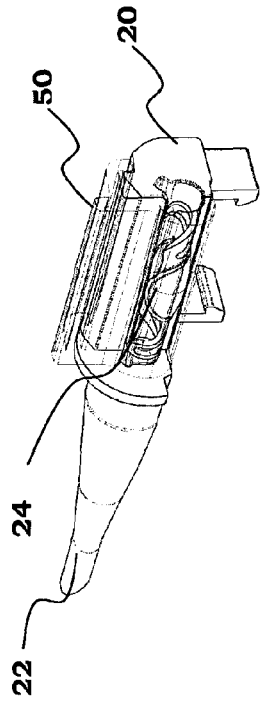

FIG. 6B shows the closed position of the cartridge 20 in which the winglet 50 is closed to the cartridge 20 causing the IOL 24 to fold. In the closed position the interior of the cartridge 20 together with the interior of the winglet 50 form a tubular inner space co-axial to the nozzle tube 22.

Although one preferred embodiment of the present invention has been illustrated in the accompanying drawings and described in the foregoing detailed description, it is understood that the invention is not limited to the disclosed embodiment but is capable of numerous rearrangements, modifications, and substitutions for IOL injectors without departing from the invention.

The invention claimed is:

1. A preloaded injector for storing and injecting hydrophobic intra ocular lenses, IOL, comprising a) an injector body accommodating a plunger placed within the injector body, b) a cartridge with a nozzle tube attached to the injector body, and furnished with a winglet having an open and a closed position, holding the IOL in a released state in case of the open position and holding the IOL in a folded position in case of the closed position, c) a stopper received into a hole defined by the injector body and preventing the plunger from reciprocating in the injector body and from entering the cartridge prior to injecting, characterized in that, a lower portion of the stopper can be plugged into a hole of the injector body through an adapter provided between the cartridge and a rotatable member, the rotatable member is provided around the cartridge, the rotatable member having a first position and a second position, where the rotatable member rotates about a longitudinal axis of the rotatable member from the first position to the second position to cause the IOL to fold into the folded position, the winglet of the cartridge is set from the open position to the closed position, when the rotatable member is rotated from the first position to the second position, and the rotatable member is furnished with a portion interfering with a portion of the stopper keeping the stopper immobilized when the rotatable member is in its first position but releasing the stopper when the rotatable member is in its second position, and the adapter and the rotatable member are removable from the injector in the closed position of the winglet.

2. The preloaded injector of claim 1, characterized in that, the adapter is furnished with rails both for connection to the injector body and to the rotatable member.

3. The preloaded injector of claim 2, characterized in that, the rail to the injector body is a groove fitting to a feather on the injector body longitudinal to the axis of the injector.

4. The preloaded injector of claim 2, characterized in that, the rail to the rotatable member is a ring shaped stop-shoulder around the outer surface of the adapter.

5. The preloaded injector of claim 1, characterized in that, the interfering portion of the rotatable member is implemented as a recess at an edge of the rotatable member, the interfering portion of the stopper is implemented as a protrusion on the leg of the stopper, and the recess on the edge of the rotatable member is positioned just above the protrusion of the stopper when turning the rotatable member to its second position.

* * * * *